(12) United States Patent
Sanders et al.

(10) Patent No.: US 12,016,583 B2
(45) Date of Patent: Jun. 25, 2024

(54) TONGUE RETRACTOR

(71) Applicant: Linguaflex, Inc., Pittsburgh, PA (US)

(72) Inventors: Ira Sanders, Oakland, NJ (US); Jon Buzzard, Boca Raton, FL (US); Asif Amirali, New York, NY (US); Cliff Dwyer, Weston, FL (US)

(73) Assignee: Linguaflex, Inc., Pittsburgh, PA (US)

( * ) Notice: Subject to any disclaimer, the term of this patent is extended or adjusted under 35 U.S.C. 154(b) by 1212 days.

(21) Appl. No.: 16/468,817

(22) PCT Filed: Dec. 13, 2017

(86) PCT No.: PCT/US2017/066132
§ 371 (c)(1),
(2) Date: Jun. 12, 2019

(87) PCT Pub. No.: WO2018/112046
PCT Pub. Date: Jun. 21, 2018

(65) Prior Publication Data
US 2020/0069320 A1 Mar. 5, 2020

Related U.S. Application Data

(60) Provisional application No. 62/433,509, filed on Dec. 13, 2016.

(51) Int. Cl.
*A61B 17/24* (2006.01)
*A61F 5/56* (2006.01)
(Continued)

(52) U.S. Cl.
CPC .............. *A61B 17/24* (2013.01); *A61F 5/566* (2013.01); *A61B 2017/00814* (2013.01);
(Continued)

(58) Field of Classification Search
CPC ............ A61B 17/0401; A61B 17/0218; A61B 17/06066; A61B 17/24;
(Continued)

(56) References Cited

U.S. PATENT DOCUMENTS 3,517,669 A 6/1970 Buono et al.
3,659,612 A 5/1972 Shiley et al.
(Continued)

FOREIGN PATENT DOCUMENTS

DE 19756956 C1 7/1999
JP 200060862 A 2/2000
(Continued)

OTHER PUBLICATIONS

WIPO (Year: 2005), WO 2005/082452 A1, Sanders.*
(Continued)

*Primary Examiner* — Camtu T Nguyen
(74) *Attorney, Agent, or Firm* — The Webb Law Firm

(57) ABSTRACT

A tissue retractor including a head member, an anchor member, and a shaft extending between the head member and the anchor member. The shaft has an elastic portion and an adjustment portion. The elastic portion is made of a first material and the adjustment portion is made of a second different material. The adjustment portion has a first locking element and the anchor member has a second locking element. The first locking element and the second locking element are configured to adjust the length of the shaft that extends between the head member and the anchor member. Also, a tissue retractor including a head member having a window and an anchoring segment surrounding the perimeter of the window, an anchor member, and a shaft extending between the head member and the anchor member, the shaft having an elastic portion and an adjustment portion.

21 Claims, 11 Drawing Sheets

(51) Int. Cl.
*A61B 17/00* (2006.01)
*A61B 17/04* (2006.01)

(52) U.S. Cl.
CPC ............... *A61B 2017/00907* (2013.01); *A61B 2017/0409* (2013.01); *A61B 2017/0417* (2013.01); *A61B 2017/0464* (2013.01); *A61B 2017/248* (2013.01)

(58) Field of Classification Search
CPC ........... A61B 2017/00814; A61B 2017/00907; A61B 2017/0409; A61B 2017/0417; A61B 2017/0464; A61B 2017/248; A61B 2017/0461; A61B 2017/06042; A61B 2090/3966; A61F 5/566
See application file for complete search history.

(56) References Cited

U.S. PATENT DOCUMENTS

| | | |
|---|---|---|
| 4,254,774 A | 3/1981 | Boretos |
| 4,335,723 A | 6/1982 | Patel |
| 4,387,879 A | 6/1983 | Tauschinski |
| 4,704,111 A | 11/1987 | Moss |
| 4,796,612 A | 1/1989 | Reese |
| 4,907,602 A | 3/1990 | Sanders |
| 4,981,477 A | 1/1991 | Schon et al. |
| 5,109,850 A | 5/1992 | Blanco et al. |
| 5,190,053 A | 3/1993 | Meer |
| 5,250,049 A | 10/1993 | Michael |
| 5,269,809 A | 12/1993 | Hayhurst et al. |
| 5,364,410 A | 11/1994 | Failla et al. |
| 5,376,110 A | 12/1994 | Tu et al. |
| 5,443,477 A | 8/1995 | Marin et al. |
| 5,464,395 A | 11/1995 | Faxon et al. |
| 5,480,420 A | 1/1996 | Hoegnelid et al. |
| 5,498,247 A | 3/1996 | Brimhall |
| 5,591,216 A | 1/1997 | Testerman et al. |
| 5,694,922 A | 12/1997 | Palmer |
| 5,792,067 A | 8/1998 | Karell |
| 5,797,913 A | 8/1998 | Dambreville et al. |
| 5,843,021 A | 12/1998 | Edwards et al. |
| 5,954,050 A | 9/1999 | Christopher |
| 5,961,440 A | 10/1999 | Schweich, Jr. et al. |
| 5,976,109 A | 11/1999 | Heruth |
| 5,980,557 A | 11/1999 | Iserin et al. |
| 5,988,171 A | 11/1999 | Sohn et al. |
| 5,989,244 A | 11/1999 | Gregory et al. |
| 5,997,567 A | 12/1999 | Cangelosi |
| 6,013,728 A | 1/2000 | Chen et al. |
| 6,132,384 A | 10/2000 | Christopherson et al. |
| 6,152,935 A | 11/2000 | Kammerer et al. |
| 6,161,541 A | 12/2000 | Woodson |
| 6,251,059 B1 | 6/2001 | Apple et al. |
| 6,267,775 B1 | 7/2001 | Clerc et al. |
| 6,408,851 B1 | 6/2002 | Karell |
| 6,409,720 B1 | 6/2002 | Hissong et al. |
| 6,439,238 B1 | 8/2002 | Brenzel et al. |
| 6,458,079 B1 | 10/2002 | Cohn et al. |
| 6,516,806 B2 | 2/2003 | Knudson et al. |
| 6,523,541 B2 | 2/2003 | Knudson et al. |
| 6,523,542 B2 | 2/2003 | Knudson et al. |
| 6,546,936 B2 | 4/2003 | Knudson et al. |
| 6,547,787 B1 | 4/2003 | Altman et al. |
| 6,558,321 B1 | 5/2003 | Burd et al. |
| 6,601,584 B2 | 8/2003 | Knudson et al. |
| 6,610,065 B1 | 8/2003 | Branch et al. |
| 6,618,627 B2 | 9/2003 | Lattner et al. |
| 6,636,767 B1 | 10/2003 | Knudson et al. |
| 6,636,769 B2 | 10/2003 | Govari et al. |
| 6,685,707 B2 | 2/2004 | Roman et al. |
| 6,742,524 B2 | 6/2004 | Knudson et al. |
| 6,764,446 B2 | 7/2004 | Wolinsky et al. |
| 6,921,401 B2 | 7/2005 | Lerch et al. |
| 6,955,172 B2 | 10/2005 | Nelson et al. |
| 7,052,516 B2 | 5/2006 | Cauthen, III et al. |
| 7,146,981 B2 | 12/2006 | Knudson et al. |
| 7,188,627 B2 | 3/2007 | Nelson et al. |
| 7,213,599 B2 | 5/2007 | Conrad et al. |
| 7,237,554 B2 | 7/2007 | Conrad et al. |
| 7,337,781 B2 | 3/2008 | Vassallo |
| 7,367,340 B2 | 5/2008 | Nelson et al. |
| 7,631,339 B2 | 12/2009 | Ishii et al. |
| 7,639,444 B2 | 12/2009 | Hutchins et al. |
| 7,845,356 B2 | 12/2010 | Paraschac et al. |
| 7,975,700 B2 | 7/2011 | Frazier et al. |
| 8,167,787 B2 | 5/2012 | Gillis |
| 8,172,801 B2 | 5/2012 | Adams |
| 8,186,355 B2 | 5/2012 | van der Burg et al. |
| 8,602,965 B2 | 12/2013 | Chu et al. |
| 8,733,363 B2 * | 5/2014 | Gillis ..................... A61F 2/00 128/897 |
| 9,041,153 B2 | 5/2015 | Chen et al. |
| 9,364,370 B2 | 6/2016 | Kühnel |
| 9,408,742 B2 | 8/2016 | Dineen et al. |
| 9,925,086 B2 | 3/2018 | Sanders et al. |
| 10,524,954 B2 | 1/2020 | Sanders |
| 2004/0045556 A1 | 3/2004 | Nelson et al. |
| 2005/0004417 A1 | 1/2005 | Nelson et al. |
| 2006/0207606 A1 | 9/2006 | Roue et al. |
| 2006/0235264 A1* | 10/2006 | Vassallo ................ A61B 17/24 602/902 |
| 2007/0144534 A1 | 6/2007 | Mery et al. |
| 2007/0288057 A1* | 12/2007 | Kuhnel .................. A61F 5/566 606/237 |
| 2008/0021485 A1 | 1/2008 | Catanese, III et al. |
| 2008/0027560 A1 | 1/2008 | Jackson et al. |
| 2008/0066766 A1 | 3/2008 | Paraschac et al. |
| 2008/0078412 A1 | 4/2008 | Buscemi et al. |
| 2011/0213207 A1 | 9/2011 | Frasier et al. |
| 2011/0230727 A1* | 9/2011 | Sanders .................. A61F 5/566 600/237 |
| 2011/0295059 A1 | 12/2011 | Machold et al. |
| 2014/0251343 A1 | 9/2014 | Weadock et al. |
| 2015/0223795 A1 | 8/2015 | Mariani |
| 2015/0238340 A1 | 8/2015 | Kagan et al. |
| 2016/0338872 A1 | 11/2016 | Sanders |

FOREIGN PATENT DOCUMENTS

| | | |
|---|---|---|
| JP | 3745606 B2 | 2/2006 |
| JP | 2008526286 A | 7/2008 |
| WO | 9221291 A2 | 12/1992 |
| WO | 9721385 A1 | 6/1997 |
| WO | 9900058 A1 | 1/1999 |
| WO | 9932057 A1 | 7/1999 |
| WO | 0029063 A1 | 5/2000 |
| WO | 0119301 A1 | 3/2001 |
| WO | 03092765 A2 | 11/2003 |
| WO | 2004064729 A2 | 8/2004 |
| WO | 2005044158 A1 | 5/2005 |
| WO | 2005051292 A1 | 6/2005 |
| WO | 2005082452 A1 | 9/2005 |
| WO | 2005110280 A2 | 11/2005 |
| WO | 2007064908 A2 | 6/2007 |
| WO | 2007092865 A2 | 8/2007 |
| WO | 2013082351 A1 | 6/2013 |

OTHER PUBLICATIONS

Argamaso, R.V., "Glossopexy for upper airway obstruction in Robin Sequence", Cleft Palate-Craniofac J., 1992, pp. 232-238, vol. 29, Issue 3.

Darrow, D.H. et al., "Management of sleep-related breathing disorders in children", Operative Techniques in Otolaryngology—Head and Neck Surgery, 2002, pp. 111-118, vol. 13, No. 2.

De Lorenzi, F. et al., "Glossoplexy over tracheostomy in the treatment of glossoptosis", Eur J Plast Surg, 2001, pp. 25-27, vol. 24, Issue 1.

Doghramji, K. et al., "Predictors of outcome for uvulopalatopharyngoplasty", The Laryngoscope, 1995, pp. 311-314, vol. 105, Issue 3.

(56) References Cited

OTHER PUBLICATIONS

Fearon, B. et al., "The management of long term airway problems in infants and children", Ann Otol Rhinol Laryngol, 1971, pp. 669-677, vol. 80, Issue 5.

Friedman, M. et al., "Minimally invasive single-stage multilevel treatment for obstructive sleep apnea/hypopnea syndrome", The Laryngoscope, 2007, pp. 1859-1863, vol. 117, Issue 10.

Horner, R.L., "Motor control of the pharyngeal musculature and implications for the pathogenesis of obstructive sleep apnea", Sleep, 1996, pp. 827-853, vol. 19, Issue 10.

Krespi, Y.P. et al., "Hyoid suspension for obstructive sleep apnea", Operative Techniques in Otolaryngology—Head and Neck Surgery, 2002, pp. 144-149, vol. 13, Issue 2.

Loube, D.I., "Technologic advances in the treatment of obstructive sleep apnea syndrome", Chest, 1999, pp. 1426-1433, vol. 116, Issue 5.

Mickelson, S.A. et al., "Midline glossectomy and epiglottidectomy for obstructive sleep apnea syndrome", The Laryngoscope, 1997, pp. 614-619, vol. 107, Issue 5.

Mintz, S.M. et al., "A modified geniotomy technique for obstructive sleep apnea syndrome", J Oral Maxillofac Surg, 1995, pp. 1226-1228, vol. 53, Issue 10.

Morgan, W.E. et al., "Surgical management of macroglossia in children", Arch Otolaryngol Head Neck Surg., 1996, pp. 326-329, vol. 122, Issue 3.

Nordgard, S. et al., "One-year results: Palatal implants for the treatment of obstructive sleep apnea", Otolaryngology—Head and Neck Surgery, 2007, pp. 818-822, vol. 136, Issue 5.

Powell, N.B. et al., "Radiofrequency volumetric tissue reduction of the palate in subjects with sleep-disordered breathing", Chest, 1998, pp. 1163-1174, vol. 113, Issue 5.

Proffit, W.R., "Muscle pressures and tooth position: North American whites and Australian aborigines", The Angle Orthodontist, 1975, pp. 1-11, vol. 45, Issue 1.

Riley, R.W., et al., "Surgery and obstructive sleep apnea: Long-term clinical outcomes", Otolaryngology—Head and Neck Surgery, 2007, pp. 415-421, vol. 122, Issue 3.

Rotunda, A.M. et al., "Detergent effects of sodium deoxycholate are a major feature of an injectable phosphatidylcholine formulation used for localized fat dissolution", Dermatologic Surgery, 2004, pp. 1001-1008, vol. 30, Issue 7.

Routledge, R.T., "The Pierre-Robin Syndrome: A surgical emergency in the neonatal period", Br J Plast Surg, 1960, pp. 204-218, vol. 13.

Strollo, P. et al., "Medical therapy for obstructive sleep apnea-hypopnea syndrome", Principles and Practice of Sleep Medicine, 4th Ed., 2005, pp. 1053-1065.

Treiber, E.S. et al., "Breast deformity produced by morphea in a young girl", Cutis, 1994, pp. 267-268, vol. 54, Issue 4.

Vicente, E. et al., "Tongue-base suspension in conjunction with uvulopalatopharyngoplasty for treatment of severe obstructive sleep apnea"; Long-term follow-up results, The Laryngoscope, 2006, pp. 1223-1227, vol. 116, Issue 7.

Woodson, B.T. et al., "Pharyngeal suspension suture with Repose bone screw for obstructive sleep apnea", Otolaryngology—Head and Neck Surgery, 2000, pp. 395-401, vol. 122, Issue 3.

Woodson, B.T., "A tongue suspension suture for obstructive sleep apnea and snorers", Otolaryngology—Head and Neck Surgery, 2001, pp. 297-303, vol. 124, Issue 3.

Woodson, B.T. et al., "A randomized trial of temperature-controlled radiofrequency, continuous positive airway pressure, and placebo for obstructive sleep apnea syndrome", Otolaryngology—Head and Neck Surgery, 2003, pp. 848-861, vol. 128, Issue 6.

* cited by examiner

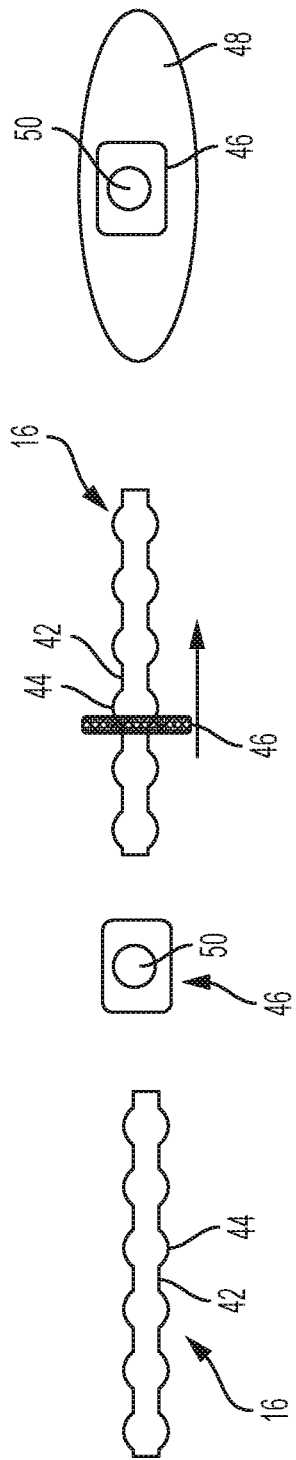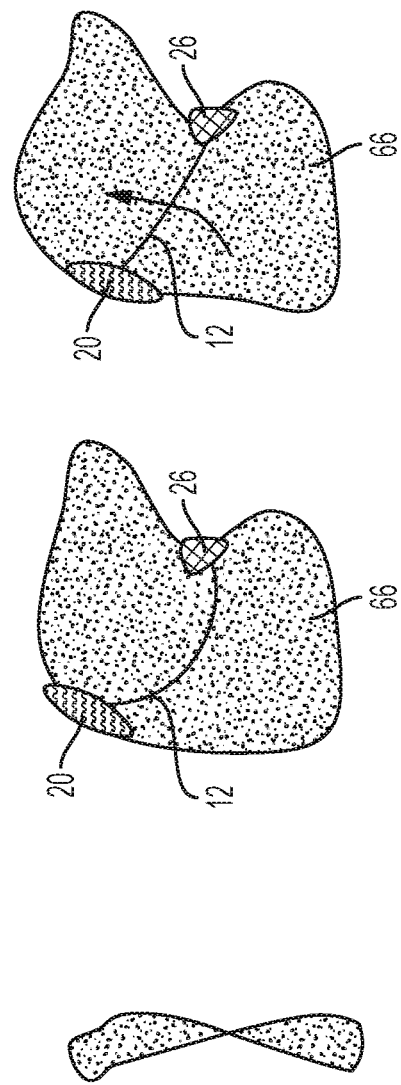

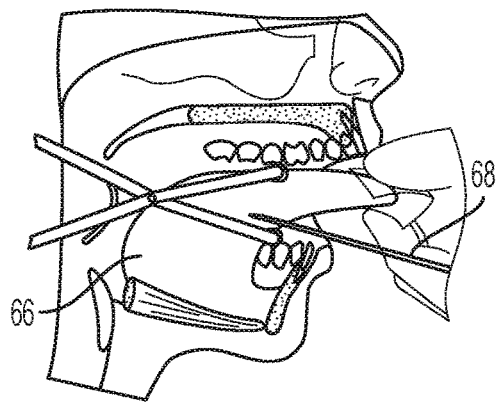
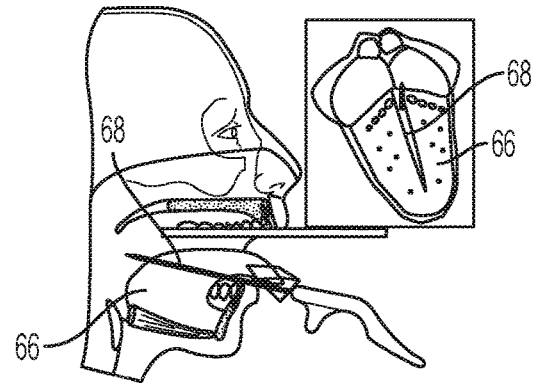
FIG. 10A  FIG. 10B
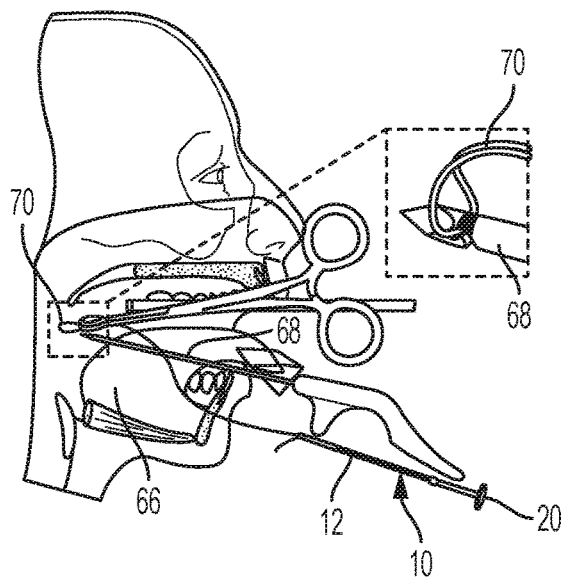
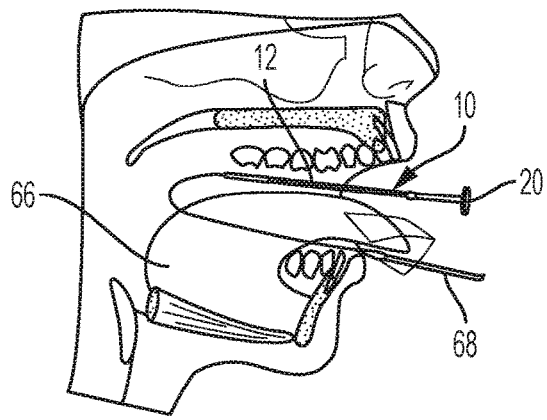
FIG. 10C  FIG. 10D

TONGUE RETRACTOR

CROSS-REFERENCE TO RELATED APPLICATIONS

This application is the United States national phase of International Application No. PCT/US2017/066132 filed Dec. 13, 2017, and claims priority to United States Provisional Application Ser. No. 62/433,509 filed on Dec. 13, 2016, the disclosures of which are hereby incorporated by reference in their entirety.

BACKGROUND OF THE INVENTION

Field of the Invention

The present invention is directed to a tissue retractor and, more specifically, to a tissue retractor for implantation in the soft tissue of the mouth in order to treat breathing disorders such as snoring, upper airway resistance syndrome, and obstructive sleep apnea syndrome (OSAS).

Description of Related Art

Snoring, upper airway resistance syndrome, and obstructive sleep apnea syndrome (OSAS) are all breathing disorders related to narrowing of the upper airway during sleep. Approximately 18 million Americans have sleep disordered breathing, but fewer than 50% are presently being diagnosed. More than 50% of Americans over age 65 have sleep difficulties, and prevalence of sleep problems will therefore increase as the over-65 population increases. Each year, sleep disorders, sleep deprivation, and excessive daytime sleepiness add approximately $16 billion annually to the cost of health care in the U.S., and result in $50 billion annually in lost productivity.

Sleep disorders are largely caused by too much soft tissue in the throat. Humans are unique because their upper airway has a curved shape, an anatomical change that is related to the evolution of human speech. As a result, the upper airway of humans is more flexible than other species and is more prone to collapse under negative pressure. In the awake state, a certain amount of tone is present in upper airway muscles to prevent this collapse. However, during sleep, muscle tone decreases in upper airway muscles and in certain susceptible individuals this relaxation allows the airway to collapse (Horner R. L., Motor control of the pharyngeal musculature and implications for the pathogenesis of obstructive sleep apnea, Sleep, vol. 19, pp. 827-853, 1996).

During inspiration, the chest wall expands and causes negative pressure to draw air into the nose and mouth and past the pharynx into the lungs. This negative pressure causes upper airway soft tissue to deform, further narrowing the airway. If the airway narrows enough, the air flow becomes turbulent causing the soft palate to vibrate. The vibration of the soft palate produces the sound known as snoring. Snoring is extremely common effecting up to 50% of men and 25% of women.

A small amount of decreased airflow or brief obstructions occurs in all humans during sleep. These episodes are counted as medically significant if airflow is decreased more than 50% of normal (hypopnea) or if airflow is obstructed for more than 10 seconds (apnea). The number of apneas and hypopneas that occur during each hour of sleep is measured to diagnose the severity of the sleep disorder. These episodes of hypopnea or apnea often cause some degree of arousal during sleep. Although the patient does not awaken to full consciousness, the sleep pattern is disturbed causing the patient to feel sleepy during the day. If the frequency of hypopnea or apnea is more than 5 episodes an hour it is called upper airway resistance syndrome. These patients often show symptoms related to the sleep disruption. Specifically, these patients are excessively sleepy during the day. In addition, more subtle symptoms such as depression and difficulty concentrating are also common.

The diagnosis of OSAS is defined as an average of more than 10 episodes of hypopnea or apnea during each hour of sleep. Although the airway is obstructed, the patient makes repeated and progressively more forceful attempts at inspiration. These episodes are largely silent and characterized by movements of the abdomen and chest wall as the patient strains to bring air into the lungs. Episodes of apnea can last a minute or more, and during this time the oxygen levels in the blood decrease. Finally, either the obstruction is overcome, usually producing a loud snore, or the patient awakes with the feeling of choking. Common symptoms in OSAS patients are morning headaches and acid reflux. Most importantly, sleep disorders can cause serious medical problems and death. Apneas cause a large strain on the heart and lungs. Over time repeated episodes of apnea cause chronic changes leading to hypertension. Long periods of apnea allow the oxygen levels in the blood to decrease. In turn, the low oxygen can cause heart attacks or strokes.

While physical stents could be used to treat these breathing disorders, their use is not practical and indirect stenting of the upper airway with positive air pressure is the most commonly prescribed treatment. This method is called continuous positive airway pressure (CPAP). CPAP requires the use of a mask tightly attached around the nose and connected to a respirator. The exact amount of positive pressure is different for each patient and must be set by overnight testing using multiple pressures. The positive pressure acts like a stent to keep the airway open. CPAP is not a cure, but a therapy that must be used every night. Although many patients are helped by CPAP, it is not comfortable for the patient or their bed partner. Patients often cannot tolerate the claustrophobic feeling of a mask tightly attached to their face. In addition, there are often many technical problems with maintaining a proper seal of the mask to the face. For these reasons, up to half of all patients who are prescribed CPAP stop using it within 6 months (Sanders, Medical Therapy for Sleep Apnea, Principles and Practice of Sleep Medicine, 2nd Edition, pp. 678-684).

The only completely effective surgical therapy for OSAS is to bypass the entire upper airway by performing a permanent tracheotomy, a surgical procedure that forms a direct connection to the trachea through the neck. This is a dangerous procedure reserved for the worst cases when there is a high risk of serious medical complications from OSAS. As the soft palate vibrates more than other tissues it plays a disproportional role in snoring. Various surgical therapies are available that shrink or stiffen the soft palate. The main procedure used is called uvulopalatopharyngoplasty [UPPP]. UPPP excises excess soft tissue of the pharyngeal walls and soft palate with a surgical scalpel. Because so much mucosa of the pharyngeal area is traumatized during a UPPP there is a large amount of post-operative swelling and severe pain. In selected patients who snore but have no obstructions more limited versions of the UPPP can be done with lasers or electrical cautery.

Newer procedures minimize trauma to the mucosa and use needles to reach the underlying soft tissue to shrink its volume or stiffen it so that it resists vibration. Electrodes can be inserted into the soft palate to deliver radiofrequency energy that shrinks or stiffens the palate (Powell, N. B., et al., Radiofrequency volumetric tissue reduction of the palate in subjects with sleep-disordered breathing, Chest, vol. 113, pp. 1163-1174, 1998) (Somnoplasty, Somus, Mountainview, CA). Mild caustic agents can be injected that decrease the volume of the soft palate. U.S. Pat. No. 6,439,238 to Benzel teaches the application of a stiffening agent to the surface of the soft palate. Most recently, office based implantation of plastic inserts to stiffen the soft palate has been approved by the FDA (U.S. Pat. No. 6,546,936: Method and Apparatus to Treat Conditions of the Naso-pharyngeal Area).

The fundamental shortcoming of all procedures that target the soft palate, including the newer techniques, is that they only partially improve OSAS (Loube, D. I., Technologic Advances in the Treatment of Obstructive Sleep Apnea Syndrome, Chest, vol. 116, pp. 1426-1433, 1999; Doghramji, K., et al. Predictors of outcome for uvulopalatopharyngoplasty, Laryngoscope, vol. 105, pp. 311-314, 1195). Although studies report a decrease in the number of apneas, these patients are rarely cured. Evidently, the critical structure causing OSAS is not the soft palate but the tongue.

The methods used to treat the tongue base in OSAS are either to permanently decrease its volume, to decrease its flexibility, or to move the entire tongue forward.

Surgical excision of the tongue base has been poorly effective. The results for scalpel or laser resection of the tongue base in OSAS treatment have not been good enough to recommend continued application of these procedures (Mickelson, S. A., Rosenthal, L., Midline glossectomy and epiglottidectomy for obstructive sleep apnea syndrome, Laryngoscope, vol. 107, pp. 614-619, 1997). More recently radiofrequency (U.S. Pat. No. 5,843,021 to Edwards at al.) and ultrasonic energy (U.S. Pat. No. 6,409,720 to Hissong et al.) have been proposed to shrink and stiffen the tongue base. The energy is delivered via needle electrodes that are inserted into the tongue base to cause a lesion that scars and shrinks over time. To avoid postoperative swelling and pain, a limited amount of lesioning is done in a single session and patients require an average of 5 treatments. About a third of patients have greater than 50% improvement in their OSAS. However, approximately a fourth of patients have significant post-operative complications, including tongue base ulcerations and abscesses, and temporary tracheotomy.

A recently introduced device for tongue base advancement is a response tongue stabilization device. The repose tongue stabilization procedure is performed under general anesthesia, and a screw is inserted at the base of the mandible. The screw contains attachments for a permanent suture that is tunneled under the mucosa of the floor of the mouth to the back of the tongue, then passed across the width of the tongue base, and brought back to attach to a metal hook screwed into the bone of the mandible. The suture is tightened to displace the tongue base forward, and caution must be observed to prevent excess tension leading to necrosis of tissue.

More aggressive surgical procedures require reconstruction of the mandible, facial, skeleton, or the hyoid bone. An example is U.S. Pat. No. 6,161,541 to Woodson et al. that teaches a method of surgically expanding the pharyngeal airway. These procedures require extensive surgery with higher risks and much longer recovery periods.

Other proposed methods for treating the tongue base include stiffening the soft tissue by injection of sclerosing particles U.S. Pat. No. 6,742,524 to Knudson et al. (Method and Apparatus to Treat Conditions of the Naso-pharyngeal Area) or other implanted material U.S. Patent Application Publication No. 2005/0004417 to Nelson et al. (Devices, Systems, and Methods to Fixate Tissue within the Regions of Body, such as the Pharyngeal Conduit).

In summary, sleep disorders are a significant health problem without an acceptable solution and there is a need in the art for new and more effective therapies.

SUMMARY OF THE INVENTION

The present invention is directed to a tissue retractor comprising a head member, an anchor member, and a shaft extending between the head member and the anchor member, the shaft comprising an elastic portion and an adjustment portion, wherein the elastic portion is made of a first material and the adjustment portion is made of a second material and the first material is different from the second material. A first end of the elastic portion of the shaft may be connected to the head member, a second end of the elastic portion of the shaft may be connected to a first end of the adjustment portion of the shaft, and a second end of the adjustment portion of the shaft may be configured to be connected to anchor member.

The adjustment portion of the shaft may have a first locking element and the anchor member may have a second locking element. When the first locking element is engaged with the second locking element, the anchor member is locked to the shaft. The first locking element may comprise a plurality of protrusions along a length of the adjustment portion of the shaft and the second locking element may comprise an opening. The force required to engage the first locking element and the second locking element may be 100-2000 grams force. The engagement of the first locking element with the second locking element may determine a length of the shaft that extends between the head member and the anchor member, and the first locking element and the second locking element may be configured to adjust a length of the shaft that extends between the head member and the anchor member.

The force required to lengthen the elastic portion of the shaft a predetermined distance may be less than the force required to lengthen the adjustment portion of the shaft the same predetermined distance, and the force required to increase a length of the elastic portion of the shaft by 1 mm may be 1-100 grams. The elastic portion of the shaft may be made from silicone and the adjustment portion of the shaft may be made from polyurethane.

The anchor member may comprise a locking insert comprising a locking element and an anchor portion surrounding the locking insert. The locking insert may be made of a material that is different from the material from which the anchor portion is made, and may be made from the second material from which the adjustment portion is made.

The anchor member has a first top surface and a second bottom surface and the shaft may be connected to the second bottom surface. The first top surface and the second bottom surface may be curved. A stabilizing member may extend from the second bottom surface. The stabilizing member may comprise a localized area on the second bottom surface providing additional surface area to the second bottom surface and may extend along a longitudinal axis of the shaft and surround at least a portion of the shaft.

At least a portion of the head member, at least a portion of the anchor member, or at least a portion of each of the head member and the anchor member may be made of a material is radiopaque.

The present invention is also directed to a tissue retractor comprising a head member comprising a window and an anchoring segment surrounding the perimeter of the window, an anchor member, and a shaft extending between the head member and the anchor member, the shaft comprising an elastic portion and an adjustment portion, wherein the window is at least partially transparent. The window may be made of a material that is different from the material from which the anchoring segment is made.

BRIEF DESCRIPTION OF THE DRAWINGS

FIG. 6A is a side view of a section of an adjustable portion of the shaft of a tissue retractor according to the present invention;

FIG. 6B is a top view of a locking insert of a tissue retractor according to the present invention;

FIG. 6C is a side view of the section of the adjustable portion of the shaft shown in FIG. 6A engaged with the locking insert of FIG. 6B;

FIG. 6D is a top view of a locking insert surrounded by an anchoring segment of an anchor member of a tissue retractor according to the present invention;

FIG. 7A is a side view of a ribbon shaped shaft of a tissue retractor according to the present invention;

FIG. 7B is a side view of the ribbon shaped shaft of FIG. 7A implanted in the base portion of the tongue prior to tensioning;

FIG. 7C is a side view of the ribbon shaped shaft of FIG. 7A implanted in the base portion of the tongue after tensioning;

FIG. 10A is a cross-section view of a first step in the implantation of a tissue retractor according to the present invention;

FIG. 10B is a cross-section view of a second step in the implantation of a tissue retractor according to the present invention;

FIG. 10C is a cross-section view of a third step in the implantation of a tissue retractor according to the present invention;

FIG. 10D is a cross-section view of a fourth step in the implantation of a tissue retractor according to the present invention;

DESCRIPTION OF THE INVENTION

As used herein, unless otherwise expressly specified, all number such as those expressing values, ranges, amounts, or percentages may be read as if prefaced by the word "about", even if the term does not expressly appear. Any numerical range recited herein is intended to include all sub-ranges subsumed therein. For example, a range of "1 to 10" is intended to include any and all sub-ranges between and including the recited minimum value of 1 and the recited maximum value of 10, that is, all sub-ranges beginning with a minimum value equal to or greater than 1 and ending with a maximum value equal to or less than 10, and all sub-ranges in between, e.g., 1 to 6.3, or 5.5 to 10, or 2.7 to 6.1. Plural encompasses singular and vice versa. When ranges are given, any endpoints of those ranges and/or numbers within those ranges can be combined with the scope of the present invention. "Including", "such as", "for example" and like terms means "including/such as/for example but not limited to".

The present invention is directed to a tissue retractor for the treatment of breathing disorders, such as snoring, upper airway resistance syndrome, and obstructive sleep apnea syndrome.

Figure 4:
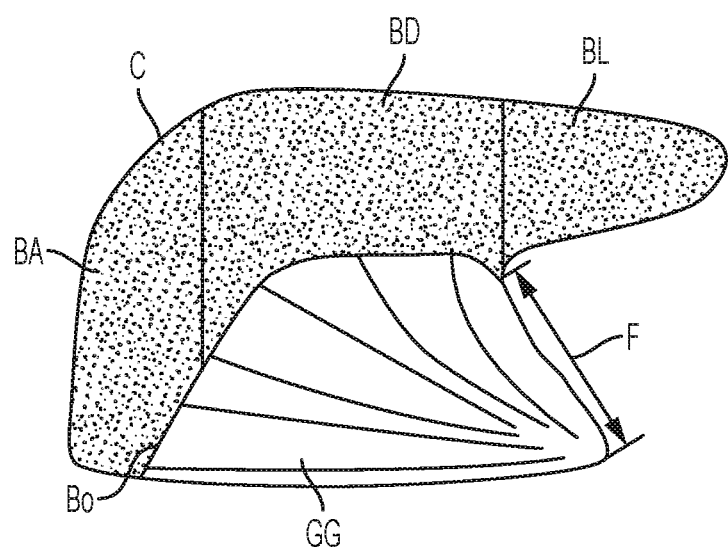
FIG. 4 is a side schematic view of the soft tissue of the mouth.

While not wishing to be bound by theory, the initial inciting event in reduction of the airway in these disorders is the deformation of a relatively small part of the tongue. The basic anatomy of the soft tissue of the mouth is shown in FIG. 4. The soft tissue includes the tongue base BA, the tongue body BD, the tongue blade BL, the curved section of the tongue base C, the boundary between the genioglossus muscle GG and the tongue Bo, and the frenulum F. Under certain conditions, deformation begins in the soft tissue on the top of the tongue, particularly in the area of the tongue curve C (see FIG. 4), and specifically near the centerline of the tongue curve C. As this tissue deforms, it narrows the airway and causes more negative pressure, thereby causing greater deformation. This feedback cycle in turn deforms enough tissue in the area to cause a complete obstruction.

If an initial obstruction occurs near the end of inspiration, the obstruction is relieved by an expiration, or by action of the genioglossus muscle GG. However, if the obstruction occurs at the beginning of inspiration reflexes trigger stronger inspiratory effort that further lowers airway pressure. This increased negative pressure causes deformation and collapse of most of the tongue base BA. At this point, the airway is firmly blocked by soft tissue and activity of the genioglossus GG only stretches the tongue tissue that is blocking the airway and cannot dislodge it.

Therefore, the tongue curve C initiates the cascade leading to obstruction. This relaxed muscle is very flexible and easy to deform, however, the converse is also true, and very little force is needed to prevent this deformation. Therefore, if sufficient counterforce is exerted at the proper localized area of the tongue, the retraction of the tissue caused by the counterforce can prevent obstruction without noticeable effects on speech and swallowing movements.

Figure 1:
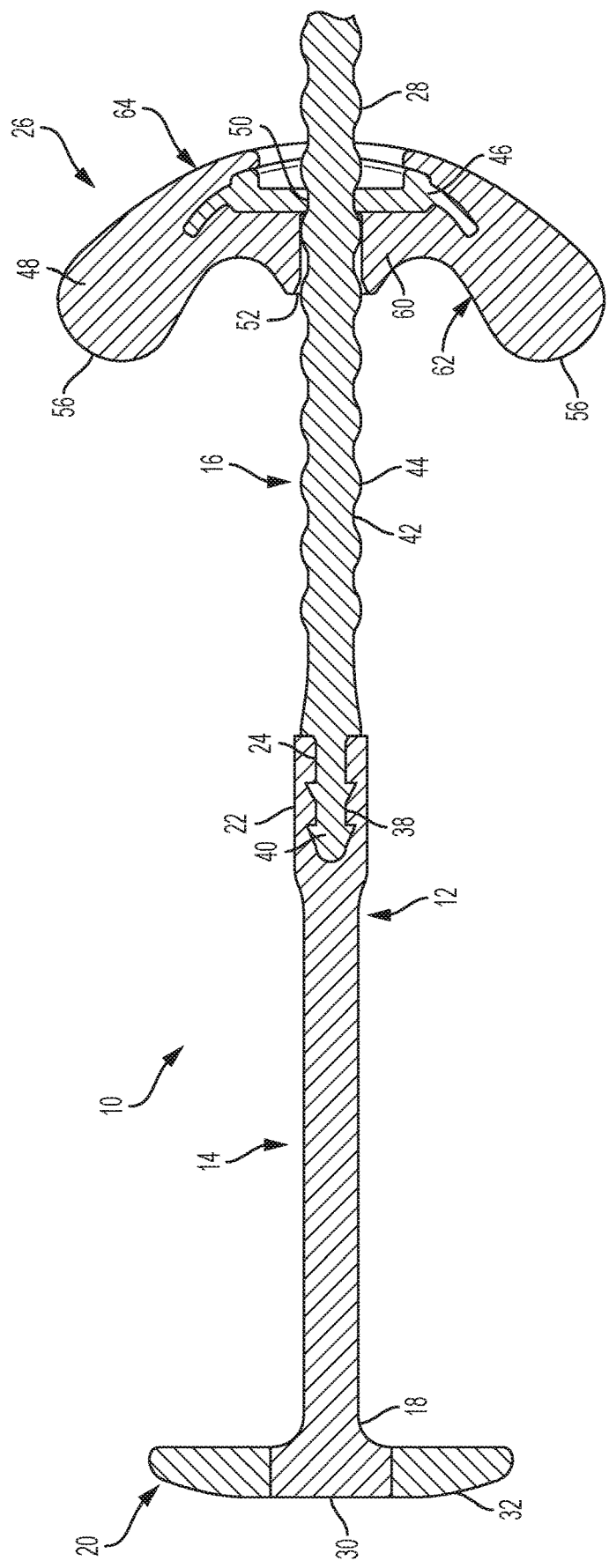
FIG. 1 is a cross-section view of a tissue retractor according to the present invention.
Figure 2:
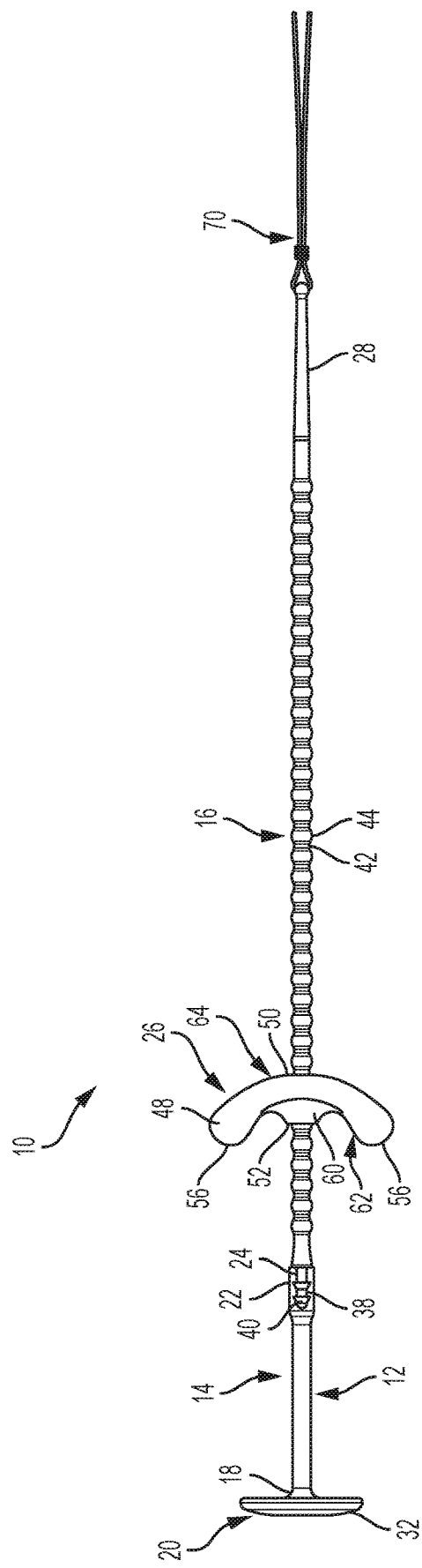
FIG. 2 is side view of a tissue retractor according to the present invention.
Figure 3:
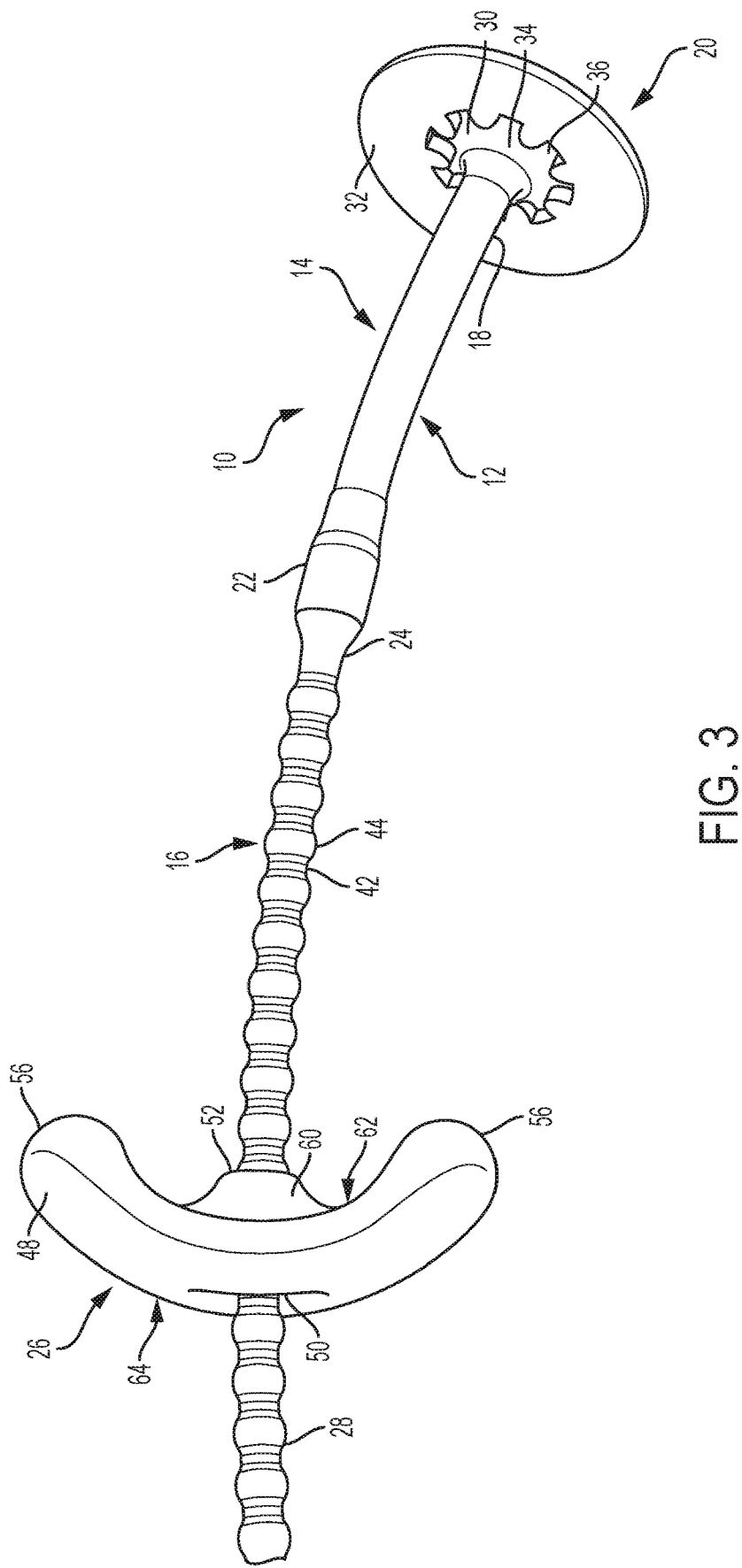
FIG. 3 is a perspective view of a tissue retractor according to the present invention.

As shown in FIGS. 1-3, the inventive tissue retractor 10 comprises a shaft 12 having an elastic portion 14 and an adjustment portion 16. A first end 18 of the elastic portion 14 of the shaft 12 is attached to a head member 20 and a second end 22 of the elastic portion 14 of the shaft 12 is attached to a first end 24 of the adjustment portion 16 of the shaft 12. An anchor member 26 is provided for attachment to a second end 28 of the adjustment portion 16 of the shaft 12.

As shown in FIG. 4, when the tissue retractor 10 is implanted in the soft tissue of the tongue base BA, the head member 20 and the anchor member 26 rest on an exterior surface of the soft tissue and the shaft 12 extends through the soft tissue. By shortening the overall length of the shaft 12 using the adjustment portion 16 of the shaft 12 and the anchor member 26, the tensile force applied to the shaft and the amount of retraction applied to the soft tissue by the head member and the anchor member can be set to the desired level, thereby exerting sufficient counterforce on the soft tissue to prevent restriction of the airway.

Figure 5A:
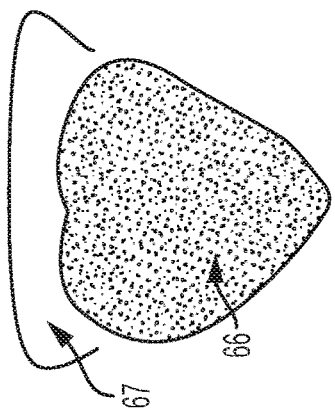
FIG. 5A is top view of the tongue and pharyngeal airway of a normal patient.
Figure 5B:
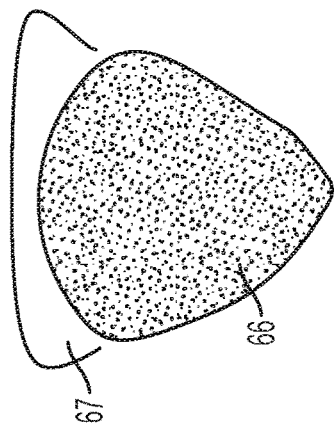
FIG. 5B is top view of the tongue and pharyngeal airway of a patient with obstructive sleep apnea.
Figure 5C:
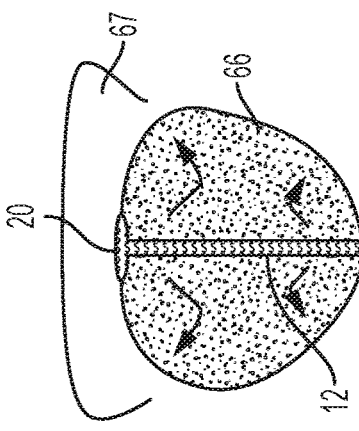
FIG. 5C is top view of the tongue and pharyngeal airway with a tissue retractor according to the present invention implanted along the tongue centerline.
Figure 5D:
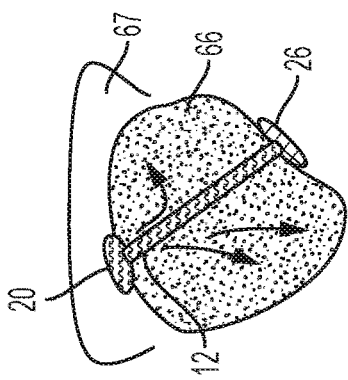
FIG. 5D is top view of the tongue and pharyngeal airway with a tissue retractor according to the present invention implanted diagonally in the tongue.
Figure 5E:
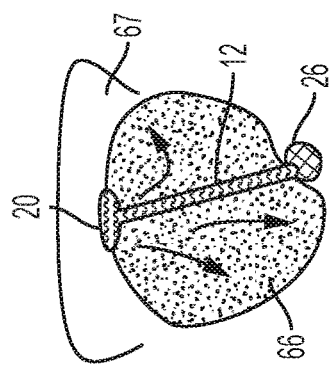
FIG. 5E is top view of the tongue and pharyngeal airway with an alternative tissue retractor according to the present invention implanted diagonally in the tongue.

In order to treat a breathing disorder such as obstructive sleep apnea, the tissue retractor 10 is implanted in the tongue 66 where it displaces volume from the tongue base BA. The head member 20 is positioned on the exterior surface of the soft tissue at the back of the tongue base BA nearest the throat and acts to retract the tongue volume out of the pharyngeal airway 67. This volume is moved to the various areas around the head member 20 and to a limited extent toward the front of the tongue 66. The anchor member 26 is positioned on the exterior surface of the soft tissue at the front of the tongue base BA nearest the front of the mouth. The shaft 12 extends through the soft tissue of the tongue base BA between the head member 20 and the anchor member 26. The length of the shaft 12 determines the amount of compressive force that is placed on the tongue volume surrounding the head member 20 and the anchor member 26. In one such implantation, the tissue retractor 10 is implanted along the tongue 66 centerline with the head member 20 and the anchor member 26 directly opposite one other (FIG. 5C). This arrangement compresses tissue between the two elements, thereby preventing volume displacement along the centerline axis and opening the pharyngeal airway 67. Alternatively, the head member 20 and the anchor member 26 may be placed diagonally from one another, for example, with the anchor member at the junction of frenulum and tongue blade BL as shown in FIGS. 5D and 5E. This arrangement causes displacement of the tissue lateral to the centerline axis in the forward portion of the tongue, allows greater volume displacement, and results in less impingement on the pharyngeal airway.

The head member 20 is adapted to rest on the exterior surface of the tissue that is being retracted by the tissue retractor 10 and anchor the first end 18 of the flexible portion 14 of the shaft 12 to the tissue. The head member 20 extends at an angle to the shaft 12 and may be substantially perpendicular to the shaft 12. In order to anchor the tissue retractor 10 to the tissue being retracted, the head member 20 is provided with a surface area that is larger than the diameter of the shaft 12. The head member 20 may take any suitable shape including, but not limited to, a disc shape having a generally circular perimeter in which the surface of the head member 20 configured to contact the tissue being retracted is circular, the thickness of the head member 20 is smaller than the diameter of the head member 20, and the diameter of the head member 20 is larger than the diameter of the shaft 12. The surface of the head member 20 may be smooth, i.e., free of protrusions or indentations, and the edges of the head member 20 may be curved in order to reduce any irritation to the tissue being retracted and/or any surrounding tissue.

The head member 20 may include a window 30 surrounded by an anchoring segment 32. The window 30 gives direct visual access to the tissue under the head member 20. The window 30 be may be at least partially transparent and may comprise a central portion 34 with at least one radial finger 36 extending therefrom. The radial fingers 36 act to increase the surface area for bonding the window 30 of the head member 20 to the anchoring segment 32 of the head member 20 and to assist in evenly distributing tension within the head member 20.

The shaft 12 may have a substantially cylindrical shape. However, at small diameters, such a cylindrical shaft 12 can cut through the soft tissue when the shaft 12 remodels tissue to form the straightest path after implantation. Therefore, at least a portion of the shaft 12 may have a ribbon shape (FIG. 7A), having a significantly wider width than its thickness, that resists remodeling of the soft tissue. The larger surface area on the flat surfaces of the ribbon shaped shaft acts as a keel. The ribbon shape may be isolated to portions of the shaft 12 or may extend along the entire length of the shaft 12. When the shaft 12 is inserted into the tongue 66 in a curved arc (FIG. 7B), the ribbon shaped shaft 12 will displace soft tissue as the tissue retractor 10 is tensioned as discussed below (FIG. 7C). The soft tissue that is displaced is determined by where the arc of the ribbon is placed and the local anatomy of the site. Therefore, different arcs and a variety of ribbon shapes can be utilized to achieve specific results.

The shaft 12 comprises a first elastic portion 14 and a second adjustment portion 16. The first end 18 of the elastic portion 14 of the shaft 12 is attached to the head member 20. The first end 18 of the elastic portion 14 of the shaft 12 may be attached to the center of the head portion 20 and may be attached to the center of the window 30 of the head member 20. The second end 22 of the elastic portion 14 of the shaft 12 is attached to the first end 24 of the adjustment portion 16 of the shaft 12. The connection between the elastic portion 14 of the shaft 12 and the adjustment portion 16 of the shaft 12 may be by mechanical engagement, chemical bonding, or a combination of the two. For example, the second end 22 of the elastic portion 14 of the shaft 12 may comprise a cavity 30 and the first end 24 of the adjustment portion 16 of the shaft 12 may comprise at least one protrusion 40 that is received in the cavity 38 in the first end 22 of the elastic portion 14 of the shaft 12. The protrusion 40 may include barbs for providing a locking engagement between the protrusion 40 and the cavity 38. In addition, the exterior of the protrusion 40 may be chemically bonded to the interior of the cavity 38.

The first elastic portion 14 of the shaft 12 is flexible and elastic, i.e., bendable and capable of elongation when subjected to a tensile force applied in the longitudinal direction of the shaft 12 as shown by the arrows in FIG. 1. In use, the elasticity of the elastic portion 14 of the shaft 12 allows for a reduction in the retraction of the soft tissue when sufficient force is applied to the tissue retractor 10. For example, when the tissue retractor 10 is implanted in the base BA of the tongue 66, the elastic portion 14 can elongate to facilitate swallowing and talking while still retracting the soft tissue of the base BA of the tongue 66 when at rest.

As shown in FIGS. 1, 2, and 7A, the adjustment portion 16 of the shaft 12 comprises central shaft 42 having a plurality of protrusions 44 extending from the central shaft 42 where the plurality of protrusions 44 have a first width or diameter, the central shaft 42 has a second width or diameter that is less than the first width or diameter of the protrusions 44, and each protrusion 44 is separated from the adjacent protrusion 44 by a portion of the central shaft 42. For example, as shown in FIGS. 1, 2, and 7, the protrusions 44 may be substantially spherical and may be separated from one another by substantially cylindrical portions of the central shaft 42. These protrusions 44 and portions of the central shaft 42 interact with the anchor member 26 to lock the anchor member 26 onto the shaft 12.

The anchor member 26 comprises a locking insert 46 (FIG. 7B) surrounded by an anchor portion 48 (FIGS. 1, 2, and 7D). The locking insert 46 has an opening 50 for receiving the adjustment portion 16 of the shaft 12 and the anchor portion 48 has a corresponding opening 52 so that the adjustment portion 16 of the shaft 12 may extend through the anchor member 26 and the anchor member 26 may be advanced along the length of the adjustment portion 16 (FIG. 7C). The opening 50 in the locking insert 46 has a diameter or width that is smaller than the diameter or width of the protrusions 44 on the adjustment portion 16 of the shaft 12. When the adjustment portion 16 of the shaft 12 is inserted into the opening 50 of the locking insert 46 with a predetermined amount of force, the opening 50 of the locking insert 46 and/or the protrusions 44 of the adjustment portion 16 of the shaft 12 deform sufficiently to allow the protrusions 44 to pass through the opening 50, thereby locking the adjustment portion 16 of the shaft 12 to the locking insert 46.

The length of the shaft 12 and the resulting tension placed on the shaft 12 may be adjusted using the locking engagement provided between the locking insert 46 and the adjustment portion 16 of the shaft 12. As more protrusions 44 pass through the opening 50 in the locking insert 46, the locking engagement between the locking insert 46 and the adjustment portion 16 of the shaft 12 is moved closer to the head member 20 and the effective length of the shaft 12 is decreased, thereby increasing the tensile force that is placed on the shaft 12. Audible and/or tactile indications may be provided as each protrusion 44 passes through the opening 50 in the locking insert 46 giving the physician implanting the tissue retractor 10 direct feedback during the locking and tensioning process. Excess length of the adjustment portion 16 of the shaft 12 may be trimmed after the locking insert 46 has been moved along the adjustment portion 16 of the shaft 12 and locked in position to achieve the desired shaft length.

The force required to deform the opening 50 in the locking insert 46 and/or the protrusions 44 of the adjustment portion 16 of the shaft 12 such that the protrusions 44 can pass through the opening 50 in the adjustment insert 46 is greater than the tensile force that will be placed on the shaft 12 tissue retractor 10 when in use. The force placed on the shaft 12 of the tissue retractor 10 in use may be at least 50 gm force, 80 gm force, or 100 gm force and may be up to 1000 gm force, 500 gm force, or 300 gm force, for example, 50-1000 gm force, 80-500 gm force, or 100-300 gm force. The amount of force needed to deform the opening 50 of the locking insert 46 and/or the protrusions 44 of the adjustment portion 16 of the shaft 12 such that the protrusions can pass through the opening may therefore be at least 100 gm force, 200 gm force, or 400 gm force and up to 2000 gm force, 1000 gm force, or 800 gm force, for example, 100-2000 gm force, 200-1000 gm force, or 400-800 gm force.

The portions of the central shaft 42 provided between the protrusions 44 may be large enough to make a significant change in shaft length and the resulting tension when the opening 50 passes over each protrusion 44, but small enough to enable reasonably precise adjustment of the shaft length and resulting tension. The distance between the protrusions 44 that is provided by the portions of the central shaft 42 may be at least 0.1 mm, at least 0.5 mm, or at least 1 mm and up to 10 mm, up to 5 mm, or up to 3 mm, for example, 0.1-10 mm, 0.5-5 mm, or 1-3 mm. Moving the locking insert 42 from one protrusion 44 to the next protrusion 44 may result in a change of tension of at least 1 gm force, at least 2 gm force, or at least 3 gm force and up to 100 gm force, up to 50 gm force, or up to 10 gm force, for example, 1-100 gm force, 2-50 gm force, or 3-10 gm force.

Alternatively, the adjustment portion 16 of the shaft 12 may have only a central shaft 42 without any protrusions and the opening 50 of the locking insert 46 may have a diameter that is smaller than the diameter of the central shaft 42 such that the adjustment portion 16 of the shaft 12 is connected to the locking insert 46 by an interference fit, thereby allowing the locking insert 46 to be placed in any position along the length of the adjustment portion 16 of the shaft 12.

The anchor portion 48 of the anchor member 26 surrounds the locking insert 46 of the anchor member 26 and includes an opening 52 such that the opening 50 provided in the locking insert 46 extends through the anchor portion 48 of the anchor member 26. The locking insert 46 may be positioned within the anchor portion 48 such that the adjustment portion 16 of the shaft 12 passes through the center of the anchor portion 48 of the anchor member 26.

The anchor portion 48 of the anchor member 26 may be any suitable shape and size such that it provides sufficient surface area to cause retraction of the soft tissue. In one aspect, the anchor portion 48 of the anchor member 26 may have a substantially circular perimeter and may be a sphere (FIG. 5E) or a disc (FIGS. 1, 2, and 5D). The anchor portion 48 may also be any intermediate shape between a sphere and a flat disc. The intermediate shapes may have perimeters of any shape that provide distribution of the force that is placed on the anchor member, for example, an oval perimeter. The anchor portion 48 may have sufficient surface area to distribute force so that no necrosis of the soft tissue occurs. The diameter or width of the anchor portion 48 of the anchor member 26 may be at least 1 mm, or at least 4 mm, or at least 8 mm and up to 40 mm, or up to 16 mm, or up to 12 mm, for example, 1-40 mm, 4-16 mm, or 8-12 mm.

It is often desirable to position the anchor member 26 on the external surface of the frenulum F. The frenulum F is a challenging surface. It is wedge shaped with a thin edge in front. This is an inherently unstable platform for an anchor member 26. It is also highly mobile. As the tongue moves forward, the frenulum F edge changes from vertical to horizontal. During chewing, the sides of the frenulum F move in all axes. The frenulum F also has some of the thinnest and most sensitive mucosa in the mouth. Underneath the mucosa are large veins draining blood from the tongue body BD and blade BL as well as sensory nerves innervating the superior tongue surface. The anchor member 26 cannot obstruct the salivary ducts which open directly at the lower part of the front edge of the frenulum F. The anchor member 26 must allow drainage from the shaft's conduit and must distribute the tension imparted to it by the head member 20 and the shaft 12 on this challenging surface.

Figure 5F:
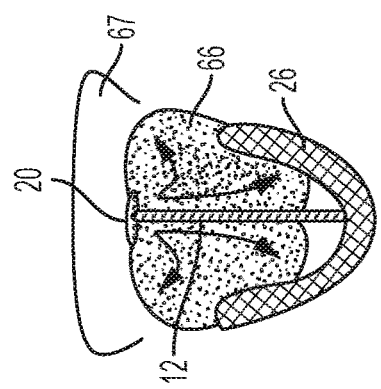
FIG. 5F is top view of the tongue and pharyngeal airway with another alternative tissue retractor according to the present invention implanted along the tongue centerline.
Figure 5G:
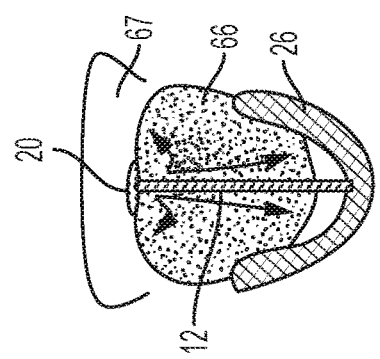
FIG. 5G is top view of the tongue and pharyngeal airway with another alternative tissue retractor according to the present invention implanted along the tongue centerline.

For placement on the frenulum F, the anchor portion of the anchor member 26 may be curved having a substantially U-shaped profile and the shaft 12 may be attached to the anchor member 26 at the midpoint or center of the anchor portion (FIGS. 1, 2, 5F, 5G, and 8). When the tissue retractor 10 is positioned with the anchor member 26 abutting the frenulum F, the ends 56 of the curved anchor member 26 bear the force of the anchor member 26 on lateral sides of the frenulum F, leaving an unloaded center where some volume of the soft tissue can be displaced (FIGS. 5F and 5G). Since high loading is placed on the ends 56 of the curved anchor member 26, the ends 56 may be bulbous and/or have an ellipsoid shape thereby increasing their surface area in order to better distribute the force and avoid tissue erosion (FIGS. 5F and 5G). Alternatively, the ends 56 of the curved anchor member 56 may be made of a deformable material such as a gel or similar material that allows the shape of the anchor portion to adapt to the underlying frenulum F.

Minimizing the amount of anchor member 26 material at the edge of the frenulum F and the top half of the frenulum F sides can increase the mobility of the frenulum F anteriorly and superiorly so that in general, the lower and farther back in the mouth the anchor member 26 is positioned the less effect it has on the normal movement of the frenulum F.

There are several alternative shapes that may be provided for the anchor member 26 that provide for placement of the anchor member 26 on the exterior surface.

Figure 8A:
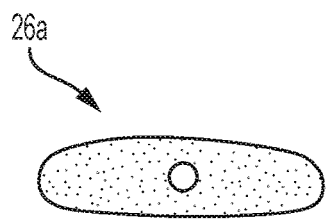
FIG. 8A is a front view of an anchor member of a tissue retractor according to the present invention.
Figure 8B:
FIG. 8B is a side view of the anchor member of FIG. 8A.

A first anchor member shape may be a bilateral symmetric shape (FIGS. 8A and 8B). As viewed from the front, the anchor portion 48a of this anchor member 26a is symmetric about its horizontal and its vertical axis such that the right and left halves of the anchor portion 48a are mirror images and the top and bottom halves of the anchor portion 48a are mirror images. As viewed from the side, the anchor portion 48a has a substantially wedge shaped cross-section that is curved at both ends.

Figure 8C:
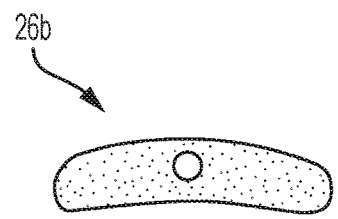
FIG. 8C is a front view of another anchor member of a tissue retractor according to the present invention.
Figure 8D:
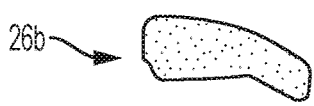
FIG. 8D is a side view of the anchor member of FIG. 8C.

A second anchor member shape may be a shape that is symmetric about only the vertical axis (FIGS. 8C and 8D). As viewed from the front, the anchor portion 48b of this anchor member 26b is symmetric about its vertical axis such that the right and left halves of the anchor portion 48b are mirror images resulting in a shape that is has a slight arc. As viewed from the side, the anchor portion 48b has an arced shape with a thicker potion curving into a thinner portion.

Figure 8E:
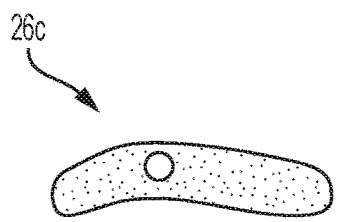
FIG. 8E is a front view of another anchor member of a tissue retractor according to the present invention.
Figure 8F:
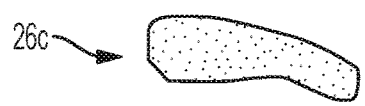
FIG. 8F is a side view of the anchor member of FIG. 8E.
Figure 8G:
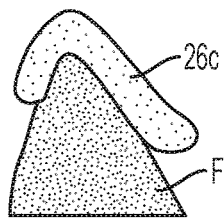
FIG. 8G is a top view of another anchor member of a tissue retractor according to the present invention.

A third anchor member shape may be a shape that is asymmetric (FIGS. 8E and 8F). As viewed from the front, the anchor portion 48c of this anchor member 26c is not symmetric about either its vertical axis or its horizontal axis such that the amount of surface area is different in the right and left halves of the anchor portion 48c and the amount of surface area in different in the top and bottom halves of the anchor portion 48c. As viewed from the side, the anchor portion 48c has an arced shape with a thicker potion curving into a thinner portion. FIG. 8G shows a bottom view of such an asymmetric anchor member 26c placed on the frenulum.

Figure 8H:
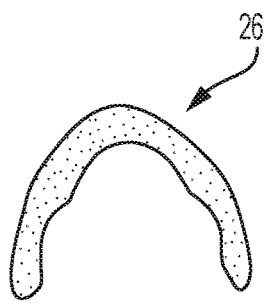
FIG. 8H is a top view of another anchor member of a tissue retractor according to the present invention.
Figure 8I:
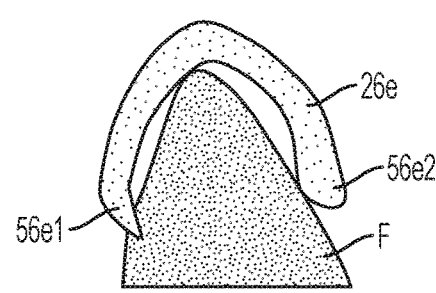
FIG. 8I is a top view of another anchor member of a tissue retractor according to the present invention.

The inner surface of the anchor member 26d may be irregular as shown in FIG. 8H. This irregular surface prevents constant pressure being placed on a nerve or a vein.

The ends 56e1, 56e2 of the anchor member 26e may also be configured to sit on the soft tissue of the frenulum F rather than push into the soft tissue. The end 56e1 in FIG. 8I having a thin cross-section that comes to a point pushes into the soft tissue. By providing an end 56e2 having a thicker cross-section with the most pointed section of end 56e2 extending outward from the outer exterior surface of the anchor member 26e, the anchor member 26e does not push into the soft tissue.

Figure 8J:
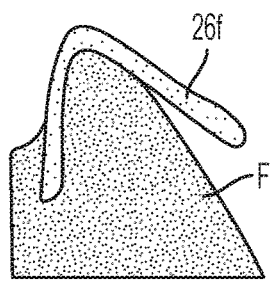
FIG. 8J is a top view of another anchor member of a tissue retractor according to the present invention.
Figure 8K:
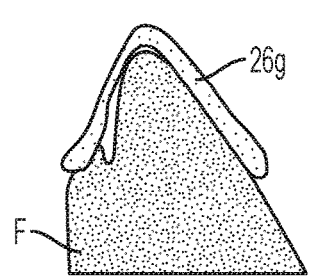
FIG. 8K is a top view of another anchor member of a tissue retractor according to the present invention.
Figure 8L:
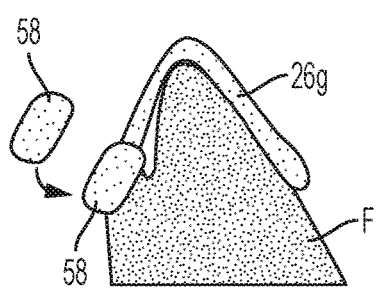
FIG. 8L is a top view of another anchor member of a tissue retractor according to the present invention.

Simply lifting the anchor member edge away from the soft tissue does not avoid the anchor member 26f digging into the soft tissue as the anchor member 26f tends to migrate back into the tissue while in use as shown in FIG. 8J. The anchor member 26g may therefore be malleable such that the portion of the anchor member 26g pushing into the soft tissue may be bent away from tissue (FIG. 8K). An extension 58 may be attached to the bent portion of the anchor member 26g to keep it from re-entering the tissue (FIG. 8L).

The head member 20 and/or anchor member 26 can migrate out of position after implantation. This largely occur because the shaft 12 is relatively thin. Such a thin linear element easily moves through the soft tissue by the so-called "cheese cutter" effect when a large amount of force is concentrated on the small surface area of the shaft 12. This causes pressure necrosis and/or remodeling of tissue. The lateral migration of the anchor member 26 can cause discomfort, because the end of the anchor member 26 may press into the soft tissue. Such migration can also decrease efficacy as the anchor member 26 moves closer to the head member 20 reducing the length of the shaft 12 and the resulting tension in the shaft 12. By distributing the force, evenly over a large surface area, migration can be minimized. This may be accomplished by providing a stabilizing member 60 or localized area of increased surface area extending from the bottom surface 62 of the curved anchor member 26 (FIGS. 1-3). The stabilizing member 60 may be radially symmetric, such as a cone shape, so that it resists movement in all directions. Alternatively, the stabilizing member 60 may be planar, such as the keel on a sailboat. A planar stabilizing member 60 allows motion in the direction of the thin edges of its flattened plane, but resists movement orthogonal to this plane. The stabilizing member 60 may be placed in interior portion of the curved anchor member 26 at the apex of the curve. A 5*5 m cone shaped stabilizing member 60 added to a curved anchor member 26 in this manner exhibited no migration in animal experimentation while migration occurred when the same curved anchor member 26 without a stabilizing member 60 was used. The location and shape of a stabilizing member 60 may also be used to maintain the orientation of the anchor member. For example, an oval anchor member 26 (see FIG. 6) can be maintained with the long axis aligned along the centerline of the tongue by a stabilizing member 60 resisting rotation. The surface area of the stabilizing member may be at least 1 mm$^2$, at least 5 mm$^2$, or at least 10 mm$^2$ and up to 1000 mm$^2$, up to 50 mm$^2$, or up to 100 mm$^2$, for example, 1-1000 mm$^2$, 5-50 mm$^2$, or 10-100 mm$^2$. The shape of the stabilizing member 60 may be conical, cylindrical, or spherical.

As shown in FIGS. 1-3, the overall shape of the anchor member 26 provided by the anchor portion 48 may have a curved bottom surface 62 and a curved top surface 64. The top surface 64 may be a bilateral symmetrical shape that is symmetric about its horizontal and its vertical axis such that the opposing halves of the anchor portion 48 are mirror images. A cone shaped stabilizing member 60 may extend from the bottom surface 62 of the anchor member 26 and may be centrally located such that the stabilizing member 60 surrounds the opening 52 provided for the adjustment portion 16 of the shaft 12.

By providing the shaft 12 with both an elastic portion 14 that has a predetermined length and an adjustment portion 16 that has a length that can be varied, the tissue retractor 10 can be adjusted to accommodate various sizes of soft tissue, for example, various sizes of tongue tissue, while providing an elastic portion 14 that insures that the force applied as the elastic portion 14 elongates is the same regardless of the size of the soft tissue in which it is implanted.

The elasticity of the elastic portion 14 of the shaft 12 allows for normal movement of the tongue as there is no specific resting position of the tongue which is almost continually active. Part of this activity involves changes in shape such as those made during speech and swallowing. Since the length of the shaft 12 determines the tension provided in the shaft 12 by the head member 20 and the anchor member 26, at least a portion of the shaft 12 must have sufficient elasticity so that the shaft 12 will return to the length set at implantation, and therefore the tension set at implantation, after it has been stretched by normal movement of the tongue. The material that is used for elastic portion 14 of the shaft 12 and the diameter or width and thickness of the elastic portion 14 of the shaft 12 determine the elasticity of the shaft.

Figure 9:
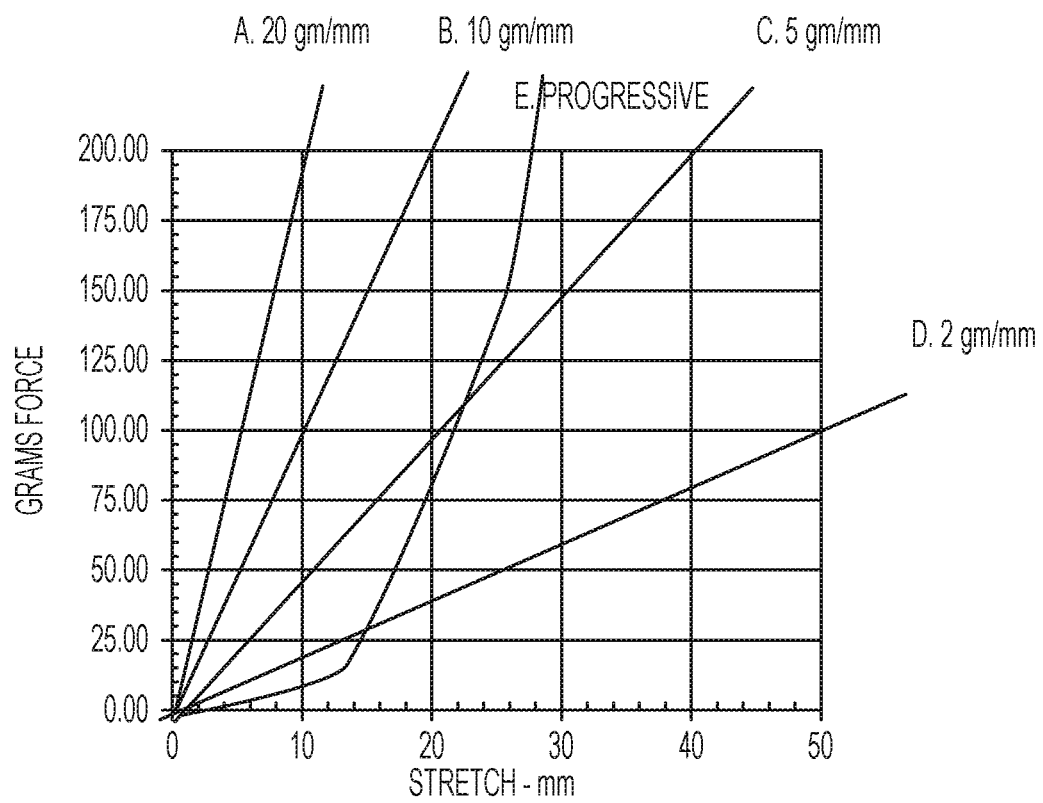
FIG. 9 is graph showing the effect of various levels of elasticity on the force that created in the elastic portion of the shaft of a tissue retractor according to the present invention.

As discussed herein, elasticity is a measure of the tensile force required to elongate an element by a certain length, for example, the tensile force in grams required to elongate an element by 1 mm. If the elastic portion 14 of the shaft 12 has low elasticity, i.e., high force is needed for a given amount of elongation, for example, 20 gm of tensile force is required to result in an elongation of 1 mm (20 gm/mm), the force required to elongate the elastic portion 14 of the shaft 12 is high and the tensile force created in the shaft 12 increases significantly when the elastic portion 14 of the shaft 12 is stretched (see FIG. 9). For example, stretching the elastic portion 14 of the shaft 12 by 1 cm can require 200 gm of force and can raise the tension in the elastic portion 14 of the shaft 12 by 200 gm. This can place excessive force on the head member 20 and/or anchor member 26, thereby causing migration or pressure necrosis. Moreover, the increased force opposes tongue extension such that the patient may feel a physical restriction on the tongue during speech or swallowing. While high elasticity at low stretch subjects the tongue to the least tension most of the time, when the tongue is stretched during obstructions the tension rises to oppose that stretch. In order to provide the needed elasticity for normal movement of the tongue without overly increasing the force placed on the head member 20 and/or the anchor member 26, the elasticity of the elastic portion of the shaft may be at least 1 gm/mm or at least 2 g/mm and may be up to 100 g/mm, up to 20 gm/mm, or up to 10 gm/mm, for example, 1-100 gm/mm, 1-20 gm/mm, or 2-10 gm/mm. Alternatively, the elasticity of the elastic portion 14 of the shaft 12 may vary depending on the amount that the elastic portion 14 of the shaft 12 is stretched. For example, the elastic portion 14 of the shaft 12 may have high elasticity, 2-10 gm/mm, in the initial 1-2 cm of stretch which rises to 20-100 gm/mm in the second 2-3 cm of stretch.

The material of the elastic portion 14 of the shaft 12 may be silicone. Silicone can be formulated in a wide variety of elasticities and the elasticity is inversely related to the shaft diameter.

However, such elastic materials are generally not well suited for applications requiring significant strength such as is needed for the locking engagement between the adjustment portion 16 of the shaft 12 and the locking insert 46 of the anchor member 26. Therefore, the adjustment portion 16 of the shaft 12 is made from a material having higher strength under tension than the material used for the elastic portion 14 of the shaft 12 and lower elasticity than the material used for the elastic portion 14 of the shaft 12, i.e., the force required to elongate the adjustment portion 16 of the shaft 12 a predetermined length is greater than the force required to elongate the elastic portion 14 of the shaft 12 the same predetermined length. This material may still be flexible, i.e., bendable, but is also resistant to tearing or notching, i.e., has low notch sensitivity, for example, polyurethane. Such a material offers the ability to provide simple locking mechanisms that are easy to use, take less space, and allow more freedom in the anchor member 26 shape.

The head member 20 and/or the window 30 of the head member 20 may be made from the same or a similar elastic material as the elastic portion 14 of the shaft 12 and may be radiopaque. For example, the elastic portion 14 of the shaft 12 and the window 30 may be made of a more elastic, clear silicone and the anchoring segment 32 of the head member 20 may be made of a less elastic silicone that is radiopaque. The more elastic silicone of the elastic portion 14 of the shaft 12 keeps forces to a minimum during stretching which minimizes long term chances of migration and improves patient comfort. The clear window 30 gives direct visual access to the tissue under the head member 20. The less elastic silicone forming the anchoring segment 32 of the head member 20 resists flexing which could cause it to collapse and enter the tongue when the tissue retractor 10 is under tension. The radiopaque silicone of the anchoring segment 32 of the head member 20 is also visible with x-ray and can be visualized if swallowed.

While the entire anchor member 26 may be made of a rigid plastic, such an anchor member 26 may be uncomfortable. Therefore, the locking insert 46 may be made of a material having higher strength and more rigidity than the anchor portion 48 of the anchor member 26. For example, the anchor portion 48 may be made of radiopaque silicone and the locking insert 46 may be made of polyether ether ketone (PEEK). The radiopaque silicone over-molded anchor portion 48 is visible with x-ray and can be visualized if swallowed. Further, the radiopaque silicone over-molded anchor portion 48 is soft, thereby improving patient comfort and minimizing unfavorable interactions with surrounding tissue. The PEEK locking insert 46 is rigid and fully surrounded by the silicone over-molded anchor portion 48. The rigid material allows for an opening 50 that will not overly distort as it is engaged with the adjustment portion 16 of the shaft 12.

Alternatively, the anchor portion 48 of the anchor member 26 may be made a soft material, such as a gel, with an underlying rigid support that may be malleable, for example, a malleable metal wire frame.

The combination of a radiopaque head member 20 in conjunction with a radiopaque anchor member 26 allows for imaging of the device with X-Ray. This provides visualization and a clear indication of the anatomical position of the shaft 12 after implantation. However, the barium additive used in the silicone to achieve radiopacity hinders durability during stretching. By having the barium only in the head member 20 and anchor member 26 any reduction in the durability of the shaft 12 is avoided.

Figure 10E:
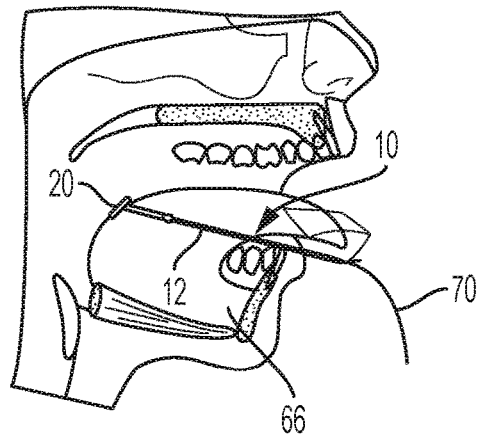
FIG. 10E is a cross-section view of a fifth step in the implantation of a tissue retractor according to the present invention.
Figure 10F:
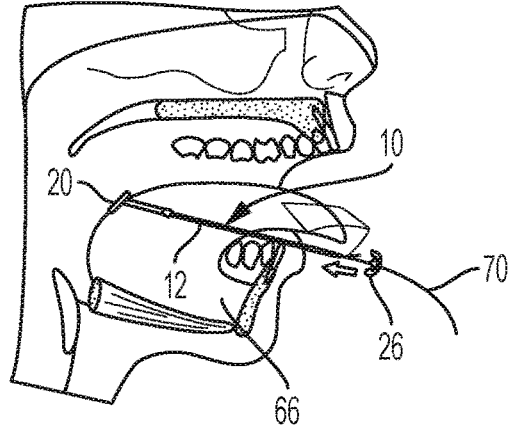
FIG. 10F is a cross-section view of a sixth step in the implantation of a tissue retractor according to the present invention.
Figure 10G:
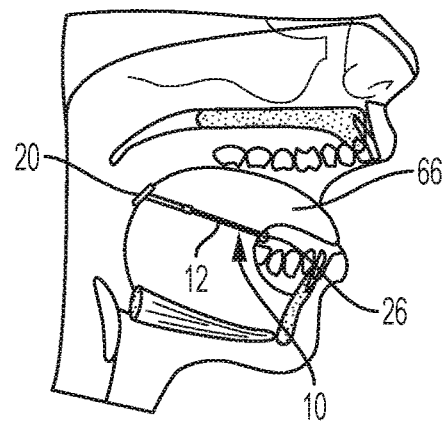
FIG. 10G is a cross-section view of a seventh step in the implantation of a tissue retractor according to the present invention.

The tissue retractor 10 is implanted into the tongue 66 by inserting a needle 68 into the midline of the tongue 66 just below the tongue blade BL and at the frenulum F (FIG. 10A). The needle 68 is passed through the tongue 66 and exits the mucosa at the posterior of the tongue 66 (FIG. 10B). A suture loop 70 is passed over the distal needle tip and pulled into the cleft of the needle 68 (FIG. 10C). The needle 68 is then withdrawn pulling the suture 70 and the tissue retractor 10 into the tongue 66 (FIGS. 10D and 10E). The anchor member 26 is then placed onto the suture 70 and advanced over the adjustment portion 16 of the shaft 12 until the anchor member 26 is in contact with the mucosa at the frenulum F and the desired tension has been applied to the shaft 12. The adjustment portion 16 of the shaft 12 is then trimmed flush with the anchor member 26.

Figure 11A:
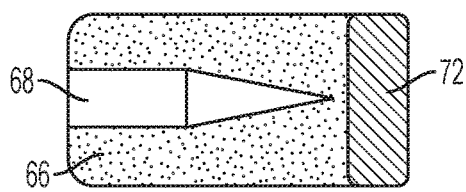
FIG. 11A is a cross-sectional view of a needle entering the tongue.
Figure 11B:
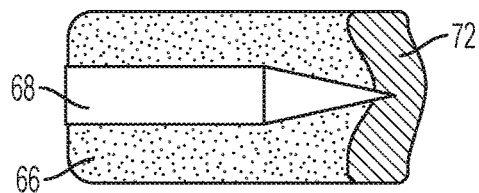
FIG. 11B is a cross-sectional view of a needle entering the tongue and tenting the mucosa.
Figure 11C:
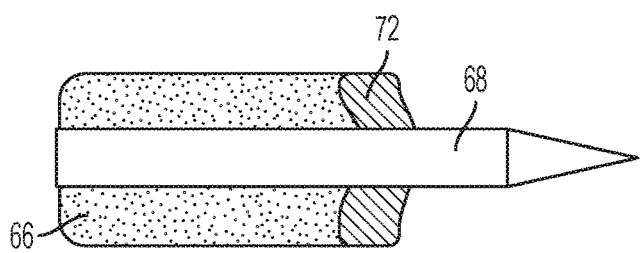
FIG. 11C is a cross-sectional view of a needle breaking through the mucosa.
Figure 11D:
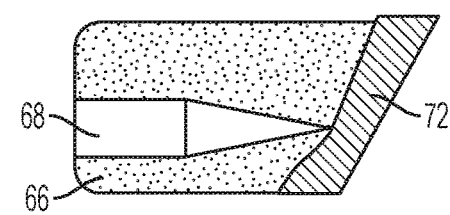
FIG. 11D is a cross-sectional view of a needle entering the tongue and obliquely contacting the mucosa.
Figure 11E:
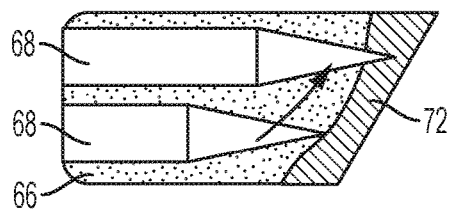
FIG. 11E is a cross-sectional view of a needle sliding along the mucosa.

However, trocar like needles penetrate base BA of tongue 66 mucosa 72 poorly. The mucosa 72 tends to tent in front of the needle 68 rather than penetrate (FIG. 11B). Then, the needle 68 penetrates the mucosa 72 quickly and with substantial force and can potentially injure the pharyngeal wall (FIG. 11C). If the needle 68 is oriented obliquely in relation to mucosa 72 to avoid this problem, the needle tip can indent rather than penetrate (FIG. 10D) the mucosa 72 and can scrape along mucosa until it penetrates (FIG. 11E) causing damage to the mucosa 72.

Figure 11F:
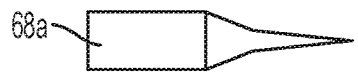
FIG. 11F is a cross-sectional view of an inventive needle.
Figure 11G:
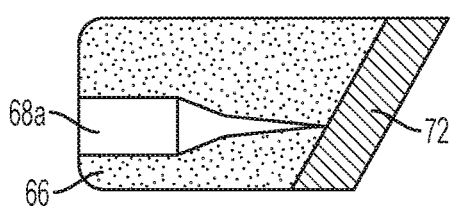
FIG. 11G is a cross-sectional view of the inventive needle entering the tongue and tenting the mucosa.
Figure 11H:
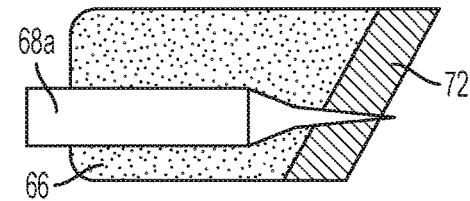
FIG. 11H is a cross-sectional view of the inventive needle breaking through the mucosa.

Both problems can be avoided by providing a needle 68a, 68b with a tip having two levels of penetrating capability. For example, the needle tip may have two portions. The first portion 74a may have an acute angle with a first maximum diameter at its base and the second portion 76a may have a larger angle with a second maximum diameter at its base (FIG. 11F), the second maximum diameter being larger than the first maximum diameter. The sharp, narrow first portion 74a penetrates the mucosa 72 easily and does not slip when penetrating oblique mucosa 72 (FIG. 11G). The needle penetrates approximately to the depth of the thickness of the mucosa 72 before being slowed by the wider second portion 76a (FIG. 11H). This prevents the uncontrolled "popping" of the needle 68a through the mucosa 72. The wider second portion 76a can then be advanced in a controlled fashion.

Figure 11I:
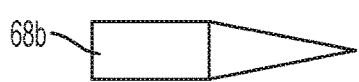
FIG. 11I is a cross-sectional view of another inventive needle.

The concept of two or more levels of needle penetration need not be limited to angles and/or diameters of the portions of the needle tip. A needle 68b having a constant angle tip could have a first portion 74b with sharp edges and a second portion 76b with dull edges (FIG. 11I).

Whereas particular aspects of this invention have been described above for purposes of illustration, it will be evident to those skilled in the art that numerous variations of the details of the present invention may be made without departing from the invention as defined in the appended claims.

The invention claimed is:

1. A tissue retractor comprising:
   a head member;
   an anchor member having a locking element; and
   a shaft having a first end and a second end and extending between the head member and the anchor member, the shaft comprising an elongated elastic portion having a first end and a second end and an elongated adjustment portion comprising a central shaft and a plurality of locking elements, the central shaft having a first end and a second end,
   wherein the elongated elastic portion is made of a first material and the central shaft of the adjustment portion is made of a second material and the first material is different from the second material,
   the elongated elastic portion of the shaft is connected to the adjustment portion of the shaft and the first end of the elongated elastic portion of the shaft corresponds to the first end of the shaft and the second end of the elongated adjustment portion of the shaft corresponds to the second end of the shaft, and
   the locking element of the anchor member selectively engages one of the plurality of locking elements of the adjustment portion to adjust a length of the shaft provided between the head member and the anchor member.

2. The tissue retractor according to claim 1, wherein the first end of the elongated elastic portion of the shaft is connected to the head member, and the second end of the elongated elastic portion of the shaft is connected to the first end of the central shaft of the elongated adjustment portion.

3. The tissue retractor of claim 1, wherein the plurality of locking elements of the elongated adjustment portion and the central shaft of the elongated adjustment portion are made from the same material.

4. The tissue retractor according to claim 1, wherein the plurality of locking elements of the elongated adjustment portion are protrusions along a length of the central shaft of the elongated adjustment portion and the locking element of the anchor member comprises an opening.

5. The tissue retractor according to claim 1, wherein a force required to engage a selected locking element of the plurality of locking elements of the elongated adjustment portion and the locking element of the anchor member is 100-2000 grams force.

6. The tissue retractor according to claim 1, wherein the head member comprises a window around the shaft, wherein the window is at least partially transparent and provides visual access to the tissue under the head member.

7. The tissue retractor according to claim 6, wherein the head member further comprises an anchoring segment surrounding a perimeter of the window and the window is made of a material that is different from the material from which the anchoring segment is made.

8. The tissue retractor according to claim 1, wherein a force required to lengthen the elastic portion of the shaft a predetermined distance is less than the force required to lengthen the elongated adjustment portion of the shaft the same predetermined distance.

9. The tissue retractor according to claim 1, wherein a force required to increase a length of the elongated elastic portion of the shaft by 1 mm is 1-100 grams.

10. The tissue retractor according to claim 1, wherein the elongated elastic portion of the shaft is made from silicone and the elongated adjustment portion of the shaft is made from polyurethane.

11. The tissue retractor according to claim 1, wherein the anchor member comprises:
a locking insert comprising the locking element; and
an anchor portion surrounding the locking insert of the locking element.

12. The tissue retractor according to claim 11, wherein the locking insert is made of a material that is different from the material from which the anchor portion is made.

13. The tissue retractor according to claim 11, wherein the locking insert is made from the second material from which the elongated adjustment portion is made.

14. The tissue retractor according to claim 1, wherein the anchor member has a first top surface and a second bottom surface, the shaft is connected to the second bottom surface, and a stabilizing member extends from the second bottom surface.

15. The tissue retractor according to claim 14, wherein the stabilizing member comprises a localized area on the second bottom surface providing additional surface area to the second bottom surface.

16. The tissue retractor according to claim 14, wherein the stabilizing member extends along a longitudinal axis of the shaft and surrounds at least a portion of the shaft.

17. The tissue retractor according to claim 1, wherein the anchor member has a first curved top surface and a second curved bottom surface and the shaft is connected to the curved second bottom surface.

18. The tissue retractor according to claim 1, wherein at least a portion of the head member, at least a portion of the anchor member, or at least a portion of each of the head member and the anchor member is made of a material that is radiopaque.

19. A method of treating a breathing disorder comprising:
providing a tissue retractor according to claim 1; and
implanting the tissue retractor into a tongue of a patient, wherein,
during the implantation of the tissue retractor, mucosal covering of the tongue is pierced, and
after implantation of the tissue retractor, the tissue retractor extends through the mucosal covering of the tongue and the shaft of the tissue retractor extends diagonally in a direction from an anterior surface of the tongue to a posterior surface of the tongue.

20. The method of claim 19, wherein the shaft of the tissue retractor extends through the tongue from the frenulum of the tongue to the tongue curve of the tongue.

21. The method of claim 20, wherein the head member of the tissue retractor is located on a posterior surface of the tongue and the anchor member is located on an anterior surface of the tongue.

* * * * *

UNITED STATES PATENT AND TRADEMARK OFFICE
CERTIFICATE OF CORRECTION

| | |
|---|---|
| PATENT NO. | : 12,016,583 B2 |
| APPLICATION NO. | : 16/468817 |
| DATED | : June 25, 2024 |
| INVENTOR(S) | : Ira Sanders et al. |

It is certified that error appears in the above-identified patent and that said Letters Patent is hereby corrected as shown below:

In the Claims

Column 18, Line 14, Claim 19, delete "mucosal" and insert -- a mucosal --

Signed and Sealed this
Seventeenth Day of September, 2024

Katherine Kelly Vidal
*Director of the United States Patent and Trademark Office*